United States Patent [19]
Runck et al.
[11] 4,397,392
[45] Aug. 9, 1983

[54] CONTAINED BLOOD GAS CONTROL

[75] Inventors: Alan H. Runck, Boston; G. Joseph Beatrice, Medford, both of Mass.

[73] Assignee: Intensive Technology, Inc., Boston, Mass.

[21] Appl. No.: 223,364

[22] Filed: Jan. 8, 1981

[51] Int. Cl.$^3$ ...................... G01N 33/96; B65D 85/00
[52] U.S. Cl. ...................................... 206/528; 53/472; 53/474; 53/484; 252/383; 252/384; 422/41; 436/11
[58] Field of Search .................................... 422/40–43; 23/230 B, 928; 53/472, 474, 484; 424/80, 359, 361; 252/316, 383, 384, 380; 206/528; 436/11

[56] References Cited

U.S. PATENT DOCUMENTS

| | | | |
|---|---|---|---|
| 1,385,075 | 7/1921 | Ferguson | 422/41 X |
| 2,797,141 | 6/1957 | Veatch | 422/42 |
| 3,136,695 | 6/1964 | Tansey | 252/316 X |
| 3,233,791 | 2/1966 | Miles | 53/474 X |
| 3,578,604 | 5/1971 | Uriel | 252/316 |
| 3,681,255 | 8/1972 | Wilfore | 23/230 B X |
| 3,944,427 | 3/1976 | Sullivan, Jr. | 252/316 X |
| 4,001,142 | 1/1977 | Turner | 23/230 B X |
| 4,250,997 | 2/1981 | Bodenmann et al. | 206/528 |
| 4,289,648 | 9/1981 | Hoskins et al. | 23/230 B X |

*Primary Examiner*—Arnold Turk
*Attorney, Agent, or Firm*—Cesari and McKenna

[57] ABSTRACT

A chemical seal for isolating the liquid phase of a contained liquid from the vapor phase present in the container headspace comprises a chemically impregnated gel formed by mixing a biopolymer gel, a high molecular weight polymer and chemical impregnants with water to form a gel-forming aqueous solution which is applied to the surface of the contained liquid and allowed to solidify thereby forming a mechanically stable, chemically impregnated gel seal in intimate contact with the contained liquid.

19 Claims, 3 Drawing Figures

12c
12b
18
16
12a
S
14
12

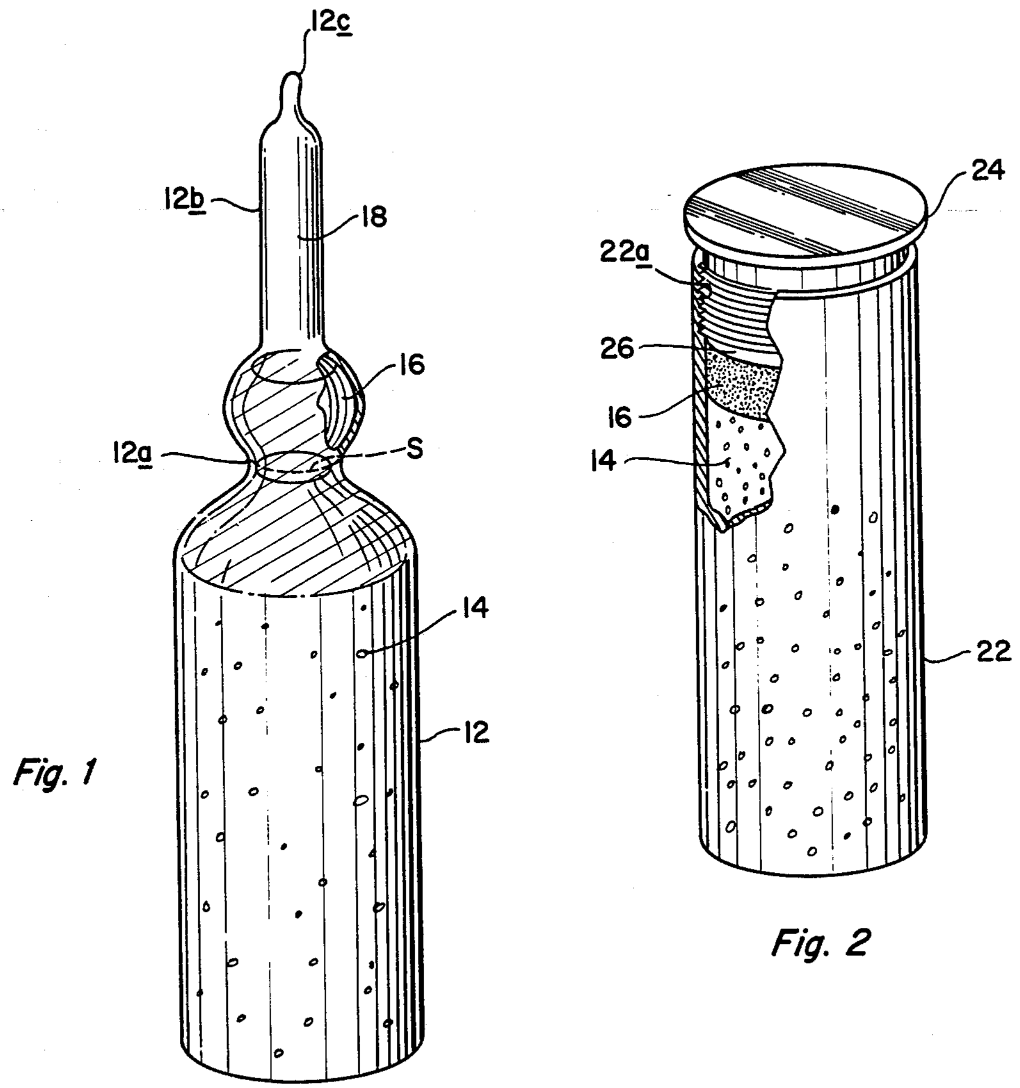

STEP 1: Combine a bio polymer gel, a high molecular weight polymer and a chemical impregnant in with water to form an aqueous solution.

STEP 2: Mix the ingredients together at an elevated temperature until all of the chemical components of the solution dissolve.

STEP 3: Carefully apply a layer of the solution over the surface of a contained liquid to be sealed.

STEP 4: Allow the container to cool so that the solution gels to a mechanically stable, chemically impregnated seal in intimate contact with the surface of the contained liquid.

CONTAINED BLOOD GAS CONTROL

This invention relates to a seal and process of preparing same. It relates more particularly to a chemical seal for isolating the gaseous and liquid phases of blood gas controls.

BACKGROUND OF THE INVENTION

When a liquid is placed in a closed container, a certain amount of headspace remains between the surface of the liquid and the container closure. In many applications, it is desirable to isolate the liquid from that headspace.

One such application of prime interest here concerns blood gas measurements which determine the pH, $pCO_2$ and $pO_2$ levels of blood specimens. These measurements which are carried out in most hospitals are often performed on arterial blood specimens on an emergency basis and the results used to assist in the selection of proper therapeutic measures for the particular patient.

Under these conditions, the instrumentation needed to perform the determinations is taken from a standby condition and used to perform these measurements. Accordingly it is especially important that quality control tests be performed in parallel with the patient specimens to assure that the blood gas instrumentation is providing accurate test data.

In other words, in order to assure that the instrument used to measure blood gas values on these specimens is accurate, reliable and precise, commercially prepared test samples should be run regularly as quality control samples.

Each control or test sample consists of a gas-equilibrated aqueous solution or cell system packaged in a sealed ampule or vial. The control liquid occupies the lower part of the ampule or vial and a gaseous headspace occupies the remainder of the vial. However, since the partition of the headspace vapor with the control liquid may change during storage because of variations in storage temperature, the headspace must be re-equilibrated with the control liquid in the vial immediately before using the sample in order to insure predictable levels of pH, $pCO_2$ and $pO_2$ of the control liquid.

This re-equilibration process is usually accomplished by vigorously shaking the vial while maintaining it at a known constant temperature. However, that procedure is troublesome for the laboratory technologist. Also, variations in the shaking technique used by the laboratory personnel can lead to inaccurate results from the blood gas measuring instrument.

An obvious solution to this problem is the complete elimination of headspace in such containers. However, this is difficult to accomplish in practice. Also, when opening such completely filled containers, it is very difficult to avoid spilling some of the container contents. Until now, then, no really effective way has been found to avoid the problem of having to re-equilibrate such blood test samples.

Organic liquid samples such as blood gas controls also have a tendency to support the growth of microorganisms which are detrimental to the effectiveness of the liquid. Therefore, it would be desirable, in addition, to inhibit such growth and thus preserve the effectiveness of the sample for a prolonged period.

SUMMARY OF THE INVENTION

Accordingly, it is an aim of the present invention to provide a technique for maintaining the stability of a contained liquid.

Another object of the invention is to provide a process for eliminating changes in equilibration between the liquid and gaseous phases of a contained liquid sample.

Another object is to provide a process for isolating a contained liquid from the container headspace.

A further object is to provide a process for forming a barrier to prevent the gas phase of a contained liquid sample from contaminating the liquid phase thereof.

Still another object is to provide a seal for isolating a contained liquid from the container headspace.

Another object of the invention is to provide such a seal which reduces the volume of gas phase in a closed container holding a measured amount of liquid phase, thereby minimizing the ability of the gas phase to contaminate the liquid phase.

Yet another object of the invention is to provide such a seal which adheres to the walls of the container so that the seal can be removed easily and completely when the liquid sample is to be used.

A further object of the invention is to provide a seal such as this which contains a chemical impregnant which maximizes the effectiveness of the liquid sample.

Other objects will, in part, be obvious and will, in part, appear hereinafter.

The invention accordingly comprises the several steps and the relation of one or more of such steps with respect to each of the others, and the composition possessing the features, properties and the relation of components which are exemplified in the following detailed disclosure, and the scope of the invention will be indicated in the claims.

In general, the aforesaid objects are achieved by applying a gel-forming solution on the surface of the contained liquid prior to closing the container. When the gel solidifies, it forms a mechanical seal or barrier between the liquid and the remaining headspace in the container. Since we are primarily interested in preserving blood gas controls which are stored in closed ampules or vials, we will describe the invention in that context. It should be understood, however, that it has equal application to the maintenance of the effectiveness of other contained liquids such as perfume and some highly soluble hydrocarbons.

The seal itself is a plural phase system. It includes a water phase which provides a common vehicle which is in intimate chemical contact with the liquid in the container (i.e. the blood sample). The second phase of the seal is a water soluble biopolymer gel phase. This component of the seal lends mechanical stability to the seal which is needed to physically isolate the liquid from the container headspace. The third phase or component of the chemical seal consists of a high molecular weight, water soluble polymer. The function of this third phase is to retard the diffusion of gas molecules through the seal, to give the seal greater mechanical stability and to create a physical bond between the edges of the seal and the inside walls of the container. The seal usually also includes a fourth phase or component, namely an impregnated chemical phase. The chemicals used in this fourth component depend upon the liquid that the seal is in contact with and the specific requirements of that liquid.

For example, in the case of a blood gas control, the control has a tendency to support the growth of certain microorganisms which are detrimental to the effectiveness of the control. To prevent such growth, the chemical phase may include water soluble antibiotics such as streptomycin which retard the growth of such microorganisms. On the other hand, where the liquid control consists of intact red blood cells which will swell and burst when in direct contact with water, i.e. the water phase of the chemical barrier, the fourth phase may include a chemical such as sodium chloride. This chemical provides an osmotic environment that is identical to the red blood cells to inhibit such swelling.

In any case, the intimate chemical contact provided by the water component of the seal assures that any chemicals impregnated in the seal also have intimate contact with the contained liquid to maximize their effectiveness.

To prepare the seal, the polymer, the gel and any chemicals to be impregnated in the seal are mixed together in distilled water to form an aqueous solution. The solution is heated and stirred to assure thorough dissolution of all of the chemical components thereof. Then the heated solution is carefully layered over the surface of the liquid sample in the container and allowed to cool. Upon cooling, the solution solidifies forming a gel seal over the surface of the sample thereby isolating it from the remaining headspace in the container. The container may be closed either before or after the formation of the gel seal.

The presence of the aforesaid chemical seal offers several very distinct and important advantages. First, it prevents the gas phase of a contained liquid sample from contaminating the liquid phase. Also to the extent that the seal reduces the headspace in the container, it reduces the volume of gas phase in the container that is capable of contaminating the liquid phase. Such a seal also prevents the contained liquid from contacting the upper portion of the container thereby improving the appearance of the container package. This is desirable from a marketing standpoint. Finally the seal, when chemically impregnated, provides a certain amount of control over the liquid sample so that the effectiveness of that sample can be preserved.

To use the sample, one simply opens the container in the usual way and removes the seal. The third or polymer component of the seal gives the seal such stability that it can be removed completely and cleanly so that there is little likelihood of it breaking apart and contaminating the liquid sample.

BRIEF DESCRIPTION OF THE DRAWING

For a fuller understanding of the nature and objects of the invention, reference should be had to the following detailed description taken in connection with the accompanying drawing, in which:

FIG. 1 is a perspective view of a contained liquid sample including a seal made in accordance with this invention;

FIG. 2 is a similar view showing the seal incorporated into a different sample container; and FIG. 3 is a block diagram showing the sequence of steps that form the sealed samples depicted in FIGS. 1 and 2.

DESCRIPTION OF THE PREFERRED EMBODIMENTS

Referring to FIG. 1 of the drawing, a small glass ampule 12 has a reduced diameter neck **12*a* and an elongated hollow stem 12*b*. The ampule 12 is filled with a liquid 14. In the embodiment specially illustrated, the liquid 14 is an arterial blood specimen taken from a patient, which specimen is introduced into the ampule through its stem 12*b*. After the ampule is filled to the level indicated, a special solution that forms a chemical seal 16 is carefully layered onto the surface of the specimen through stem 12*b*. Finally, the ampule 12 is closed by a glass weld 12*c* formed at the upper end of stem 12*b*. Seal 16 is in intimate contact with the liquid 14 and provides a barrier between that liquid and the remaining headspace 18, namely the volume inside the stem 12*b* above seal 16**.

FIG. 2 illustrates a similar seal 16 incorporated into a somewhat different container. In FIG. 2, the sample liquid 14 is introduced into a generally cylindrical glass vial 22. The upper end segment **22*a* of the vial is internally threaded as shown. After the vial is filled with liquid and the seal 16 is formed at the surface of the liquid, the vial is closed by an externally threaded glass stopper 24. As in the FIG. 1 container, the seal 16 separates the liquid 14 from the headspace 26 which exists between the upper surface of the seal 16 and the lower surface of the stopper 24**.

The chemical seal 16 comprises at least three and usually four different phases. It includes a water phase which is compatible with the blood sample that also contains water and which is therefore in intimate chemical contact with the sample. Consequently, any chemicals impregnated in the seal are also assured intimate contact with the blood sample. The second phase of the chemical seal 16 is a biopolymer gel phase. As noted above, this phase lends mechanical stability to the seal. Polymer gels which have been found to be particularly suitable in the present application are agarose and collagen. The gel should be present in an amount of from about 0.5 to 6 percent (weight per volume of solution) to provide a good mechanical barrier to prevent contact of the liquid sample with the headspace vapor in the container, about 1% being an optimum amount.

The third phase of the seal consists of a high (e.g. 100,000 units) molecular weight polymer such as polyvinylpyrrolidone (PVP), dextran or hydroxyethyl starch. This third phase retards the diffusion of gas molecules through the chemical seal 16. It also enhances the mechanical stability of the seal and creates a physical bond between the edges of the seal 16 and the sidewalls of the container 12 or 22. This component also should be present in an amount of from about 0.5 to 6 percent (weight per volume of solution), 1% being optimum. The fourth phase of the seal is the impregnated chemical phase. The chemicals used depends on the sample liquid the seal is in contact with and the special requirements that sample presents. Specific examples will be given shortly.

The aforesaid seal components or phases are mixed together in solution. The chemicals in the solution are dissolved by slowly heating the solution to an elevated temperature in the order of 30°–60° C., while stirring the solution. After the chemicals are dissolved, the solution is ready for applying to the containers previously filled with the sample liquid. Until used, the solution should be stored at that same elevated temperature to maintain it in a liquid phase.

In use, the solution is deposited carefully over the surface of the sample liquid in the container until a layer having a thickness in the order of 5 millimeters is formed. The container is then placed in a relatively low temperature environment (e.g. 0°-10° C.) so that the plural phase solution slowly but spontaneously forms a gel which thereby greatly enhances its stability and mechanical durability. Once the gel seal has formed (e.g. after about 10 minutes), the container can be closed or capped by seal 12*c* or stopper 24 and packaged in a conventional manner for transportation or storage. Actually, the container can be closed before the seal forms as long as the container is not tipped or jostled so as to upset the solution layer.

Once the gel seal is formed, it provides a durable, mechanical barrier which separates the liquid sample from the headspace in the container. The seal thus prevents contamination of the liquid phase by headspace vapors. The seal also occupies an appreciable volume of the headspace above the level of the liquid. Therefore, it minimizes the volume of the gas phase present in the container thereby minimizing its ability to contaminate the liquid phase therein. The chemical impregnant in the seal which is mated to the sample liquid prevents degradation of that liquid and thus preserves its ability to function as a reliable test sample.

When the sample illustrated in FIG. 1 or 2 is to be used, the container 12 or 22 is rolled between the hands to thoroughly mix the blood sample. Small mixing balls may, if desired, be placed in the container to help in this respect. Then the container is opened. In the case of the ampule 12, for example, this is accomplished by breaking the ampule at its neck 12*a*. Preferably, the neck is prescored as indicated at S to facilitate this. When the portion of the ampule above the score line S is removed, the seal 16 which exists as a coherent mass separates readily from the surface of the blood sample. Therefore, no seal residue or particles remain in the ampule that could contaminate the specimen. The test sample can then be used in the appropriate instrumentation in the customary way.

It should be understood at this point that, until use, the contained and sealed sample should be stored at the relatively low temperature at which the seal formed, e.g. 4° C. If the contained sample should be heated excessively, e.g. to 60° C., the gel seal will revert to its liquid phase. Since the containers are usually stored and transported on their sides, this will result in breaking the barrier between the sample liquid and the container headspace thereby spoiling the sample as far as this invention is concerned. In fact, the presence of liquid or seal-forming solution in the container headspace provides a ready indication that the headspace barrier has been breached and the samples can be discarded.

The following are specific examples of the present seal and the process of forming same:

EXAMPLE I (For use particularly with whole blood controls)

A glass vial with a capacity of approximately 3 ml was filled with approximately 2.0 ml of a suspension of preserved red blood cells or red blood cell hemolysate intended for use as a quality control sample for blood gas analysis.

A mixture of sealant solution was then prepared by adding 1.0 gram agarose, 1.0 gram polyvinylpyrrolidone (PVP), 0.9 gram sodium chloride, 100 mg tetracycline, and 200 mg methyl-p-hydrozybenzoate to distilled water and adding sufficient distilled water so that the final volume of the resulting solution was approximately 100 ml. The chemicals in the sealant solution were dissolved by slowly heating the solution to a temperature of 60° C. and stirring. After the chemicals were dissolved, the sealant solution, ready for applying to the previously filled vial, was stored at a temperature of 60° C.

A syringe fitted with an 18-guage hypodermic needle was used to apply the sealant to the vial filled with the blood specimen. The sealant solution and the syringe were kept at 60° C. prior to applying the sealant. Approximately 10 ml of the sealant solution were aspirated into the syringe and any air bubbles remaining in the syringe expelled. The syringe was then positioned over the previously filled vial so that the hypodermic needle attached to the syringe contacted the side of the filled vial above the meniscus of the blood sample in the vial. The sealant was then carefully layered over the quality control liquid in the vial by slowly depressing the syringe plunger until a layer of sealant having a thickness of approximately 5 mm formed. Next, the syringe and needle were withdrawn from the vial and returned to the 60° C. environment and the thus processed vial was placed in a 4° C. environment for about 10 minutes so that the liquid slowly but spontaneously formed a gel. Then the vial was capped. The resultant seal contained no trapped bubbles that would affect its gas-sealing capability and it remained as a coherent mass in intimate contact with the liquid sample and did not shrink or pull away from the wall of the vial. Furthermore, no microorganisms appeared in the sample.

EXAMPLE II (For use particularly with aqueous solution blood gas controls)

A glass vial with a capacity of approximately 3 ml was filled with approximately 2.0 ml of a solution of gas-equilibrated buffer solution intended for use as a quality control sample for blood gas analysis. A mixture of sealant solution was prepared as described in Example I, except that the sealant solution was composed as follows:

A mixture of sealant solution was prepared by adding 1.0 gram agarose, 1.0 gram polyvinylpyrrolidone (PVP), and 100 mg sodium azide to distilled water and adding sufficient distilled water so that the final volume of the resulting solution was approximately 100 ml. Once prepared, the solution was stored at 60° C. as described in Example I.

The prepared sealant solution was then applied to the filled via of aqueous control in the same manner described in Example I. The resultant seal possessed the same desirable characteristics as the one described in Example I.

EXAMPLE III (Using collagen as a substitute for agarose)

The methodology used for preparing the sealant solution was identical to that used in Examples I and II, except that collagen was used in place of agarose. That is, instead of adding 1.0 gram of agarose to the sealant suspension preparation, 1.0 gram of collagen was added. After preparation of the sealant solution, it was applied to the specimen in the identical manner described in Examples I and II and achieved similarly effective results.

EXAMPLE IV (Using hydroxyethyl starch as a substitute for PVP)

The methodology used for preparing the sealant solution was identical to that used in Examples I and II, except that hydoxyethyl s arch was used in place of polyvinylpyrrolidone (PVP). Instead of adding 1.0 gram of PVP to the sealant mixture during preparation, 1.0 gram of hydroxyethyl starch was added. After preparation of the sealant solution, it was applied to the specimen in the same manner described in Examples I and II. The seal that formed in the vial formed an equally effective headspace barrier.

Using the foregoing specially prepared chemical seal, then, one can maintain the effectiveness and stability of contained liquid samples. The seal is easy to prepare and easily applied to the sample. Once it is so applied, the liquid sample can be stored for a long period of time and still maintain its effectiveness as a test sample. Yet the cost of incorporating the seal into such contained samples is relatively small. Therefore the seal should find wide application in the medical field.

It will thus be seen that the objects set forth above, among those made apparent from the preceding description, are efficiently attained, and, since certain changes may be made in the above described sequence of steps and in the aforesaid construction without departing from the scope of the invention, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. A process for isolating a contained blood gas control from the remaining headspace in the container comprising partially filling a container with a blood gas control, applying an aqueous polymer gel-forming solution to the surface of the blood gas control thereby partially filling the headspace in the container and allowing the solution to form a mechanically stable, thin but nonporous, plural phase gel seal in intimate contact with the surface of the contained blood that prevents changes in equilibration between the liquid and gaseous phases of the control.

2. The process defined in claim 1 wherein the applying step is performed by injecting the solution onto an interior wall of the container just above the surface of the blood gas control so that the solution is carefully layered onto the surface of the blood gas control.

3. The process defined in claim 1 wherein the solution is maintained at an elevated temperature in excess of about 30° C. prior to its introduction into the container.

4. The process defined in claim 3 wherein said temperature is in the order of 60° C.

5. The process defined in claim 3 wherein the allowing step includes subjecting the container and its contents to a reduced temperature of between about 0° C. to 10° C.

6. The process defined in claim 5 wherein said reduced temperature is about 4° C.

7. The method defined in claim 1 and including the additional step of adding one or more chemicals to the solution to form an impregnant in the gel seal in intimate contact with the contained blood gas control.

8. A process for preparing a chemical seal for isolating the gaseous and liquid phases of a contained blood gas control comprising the steps of forming an aqueous solution of a water soluble gel, a water soluble high molecular weight polymer, the gel and polymer each being present in an amount of from 0.5 to 6 percent (weight per volume of solution); subjecting the solution to an elevated temperature sufficient to maintain it in a liquid phase until use; carefully applying the solution onto the surface of the contained blood gas control to be sealed until that surface is completely covered; and allowing the contained blood gas control and solution to cool sufficiently to cause the solution to form a mechanically stable, thin but nonporous, plural phase gel seal in intimate contact with the blood gas control thereby forming a barrier between the blood gas control and the remaining headspace in the container that prevents changes in equilibration between the liquid and gaseous phases of the control.

9. The process defined in claim 8 wherein the solution is maintained at a temperature of about 60° C. until use and cooled to a temperature of about 4° C. after it is applied to the blood gas control.

10. The process defined in claim 8 wherein a biopolymer gel selected from the group consisting of agarose and collagen and a polymer selected from the group consisting of polyvinylpyrrolidone, hydroxyethyl starch and dextran are mixed together to form said aqueous solution.

11. The process defined in claim 10 wherein the gel and polymer are each present in the amount of about one percent (weight per volume of solution).

12. The process defined in claim 8 and further including the additional step of adding to said solution one or more water soluble chemicals which impregnate the resultant gel seal so as to preserve the effectiveness of the contained blood gas control.

13. The process defined in claim 12 wherein said added chemicals include an antibiotic.

14. The process defined in claim 12 wherein the added chemicals include sodium chloride.

15. A contained blood gas control comprising a container, a volume of blood gas control partially filling the container and a chemical seal for said control formed by mixing a water soluble biopolymer gel, a water soluble high molecular weight polymer and one or more selected water soluble blood compatible chemicals in water at an elevated temperature to form an aqueous solution, the gel and polymer each being present in an amount of from 0.5 to 6 percent (weight per volume of solution), layering the solution on the surface of the contained control and allowing the solution to cool until it forms a mechanically stable, thin but nonporous, plural phase gel seal at the surface of the control which is impregnated with said chemicals, is compatible with blood, is nonporous to the blood gases in the control and prevents changes in equilibrium between the liquid and gaseous phases in the blood gas control in the container.

16. The seal defined in claim 15 wherein the biopolymer gel is selected from the group consisting of agarose and collagen.

17. The seal defined in claim 15 wherein the polymer is selected from the group consisting of polyvinylpyrrolidone, hydroxyethyl starch and dextran.

18. The seal defined in claim 15 wherein the chemicals include an antibiotic.

19. The seal defined in claim 15 wherein the chemicals include sodium chloride.

* * * * *